United States Patent [19]

Vooheis

[11] Patent Number: 5,492,812
[45] Date of Patent: Feb. 20, 1996

[54] DIAGNOSTIC METHOD FOR ALZHEIMER'S DISEASE BY SCREENING FOR TAU-PEPTIDES IN THE BLOOD OF A PATIENT

[75] Inventor: H. Paul Vooheis, Dublin, Ireland

[73] Assignee: Provost, Fellows and Scholars of Trinity College, Dublin, Ireland

[21] Appl. No.: 159,969

[22] Filed: Nov. 30, 1993

Related U.S. Application Data

[63] Continuation of Ser. No. 738,778, Aug. 1, 1991, abandoned.
[51] Int. Cl.$^6$ .................... G01N 33/53; G01N 33/537; G01N 33/543
[52] U.S. Cl. .................... 435/7.1; 435/7.92; 435/7.93; 435/7.94; 435/7.95; 436/518; 436/804; 436/811
[58] Field of Search .................... 435/7.1, 7.2, 7.21, 435/7.92, 975; 436/506, 518, 512, 811, 864, 828, 515, 516, 808

[56] References Cited

FOREIGN PATENT DOCUMENTS 1302250 6/1992 Canada.

OTHER PUBLICATIONS

Kosik et al, "Epitopes That span the Tau Molecule Are Shared with Paired Helical Filaments", Neurons 1:817–825 (Nov. 1988).
Singh et al, "Detection of Brain Autoantibodies in The Serum of Patients With Alzheimer's Disease But Not Down's Syndrome", Immunol. Lett., 12:277–280 (1986).
Gaskin et al. "Patients with Clinically Diagnosed Senile Dementia of the Alzheimer Type (SDAT) Make Autoantibodies That React with Neurofibrillary Tangles", Clin. Res., 34(2):669 A (1986).
Grundke-Iqbal et al, "Microtubule-associated Protein Tau", J. Biol. Chem., 261(13):6084–6089 (May 5, 1986).
Foley et al. "Evidence for the presence of antibodies to cholinergic neurons in the serum of patients with Alzheimer's disease", J. Neurol., 235:466–471 (1988).

Morris et al, "The Consortium to Establish a Registry for Alzheimer's Disease (CERAD)", Neurology 39:1159–1165 (1989).
Wolozin et al. "Alzheimer–Related Neuronal Protein A68: Specificity and Distribution", Ann. Neurol., 22:521–526 (1987).
Ksiezak–Reding et al, "Mapping of the Alz–50 Epitope in Microtubule–Associated Proteins Tau", J. Neurosci. Res., 25:412–419 (1990).
Ksiezak–Reding et al., 1988, "Immunochemical and biochemical characterization of τ proteins in normal and Alzheimer's disease brains with Alz 50 and Tau–1", J. Biol. Chem. 263(17):7948–7953.
Kingsley et al., 1988, "Human antibodies to neurofibrillary tangles and astrocytes in Alzheimer's disease", Neuroimmunol. 19:89–99.
Gaskin et al., 1987, "Autoantibodies to neurofibrillary tangels and brain tissue in Alzheimer's disease: Establishment of Epstein–Barr Virus–transformed antibody–producing cell lines", J. Exp. Med. 165:245–250.
Iqbal et al., 1989, "Laboratory Diagnostic tests for Alzheimer's disease", Prog. Clin. Biol. Res. 317:679–687.

Primary Examiner—Toni R. Scheiner
Assistant Examiner—Patricia A. Duffy
Attorney, Agent, or Firm—Pennie & Edmonds

[57] ABSTRACT

The present invention is directed to methods and kits for diagnosing, Alzheimer's disease. The invention is based, in part, on the discovery that proteolytic fragments of the amino and carboxy terminal amino acid residues of tau-proteins are released from the neurofibrillary tangles associated with the disease and can be detected in body fluids outside the brain. The tau-proteins will be purified or chemically synthesized and peptide fragments of the amino terminal and carboxy terminal regions will be obtained proteolytically or synthesized chemically and will be used in generating tau specific antibodies for use in diagnostic kits for the detection of Alzheimer's disease. These diagnostic kits will be used in screening the body fluids of individuals for the presence of tau-peptide fragments. Alternatively, the tau-peptides themselves may be used in diagnostic kits for screening the body fluids of individuals for the presence of circulating autoantibodies.

2 Claims, 2 Drawing Sheets

```
-37 CGGCCTCTGTCGACTATCAGGTGAACTTTGAACCAGG

1   Met Ala Glu Pro Arg Gln Glu Phe Glu Val Met Glu Asp His Ala Gly Thr Tyr Gly Leu Gly Asp Arg Lys Asp Gln Gly Gly Tyr Thr
  1   ATG GCT GAG CCC CGC CAG GAG TTC GAA GTG ATG GAA GAT CAC GCT GGT ACG TAC GGG TTG GGG GAC AGG AAA GAT CAG GGG GGC TAC ACC

31   Met His Gln Asp Thr Gly Asp Ala Gly Leu Lys Ala Gly Ile Gly Ala Gly Glu Glu Ala Gly Asp Thr Pro Ser Leu Glu Asp Glu Ala
 91   ATG CAC CAA GAC ACG GGT GAC GCT GGT CTG AAA GCT GGA ATT GGA GCA GAA GAA GCT GGA GAC ACC CCC AGC CTG GAA GAC GAA GCT

61   Ala Gly His Val Thr Gln Ala Arg Met Val Ser Lys Ser Lys Asp Gly Thr Gly Ser Asp Asp Lys Lys Ala Lys Gly Ala Asp Gly Lys
101   GCT GGT CAC GTG ACC CAA GCT CGC ATG GTC AGT AAA AGC AAA AGT GAT GGA ACT GGA AGC GAT GAC AAA AAA GCC AAG GGT GCT GAT GGC AAA

91   Thr Lys Ile Ala Thr Pro Arg Gly Ala Ala Pro Pro Gly Gln Lys Gly Gln Ala Asn Ala Thr Arg Ile Pro Ala Lys Thr Pro Pro Ala
271   ACG AAG ATC GCC ACA CCG CGG GGA GCA GCC CCT GGT CAA AAG GGC CAG GCT AAC GCC ACC AGG ATT CCA GCA AAA ACC CCG CCC GCT

121   Pro Lys Thr Pro Pro Ser Ser Gly Glu Pro Pro Lys Ser Gly Asp Arg Ser Gly Tyr Ser Ser Pro Gly Ser Pro Gly Thr Pro Gly Ser
361   CCA AAG ACA CCA CCC AGC TCT GGT GAA CCT CCA AAA TCA GGC GAT CGC AGC GGC TAC AGC AGC CCC TCC CCA GGC ACT CCC GGC AGC

151   Arg Ser Arg Thr Pro Ser Leu Pro Thr Pro Pro Thr Arg Glu Pro Lys Lys Val Ala Val Val Arg Thr Pro Pro Lys Ser Pro Ser Ser
451   CGC TCC CGC ACC CCG TCC CTT CCA ACC CCA CCC ACC CGG GAG CCC AAG AAA GTG GCA GTG GTC CGT ACT CCA CCC AAG TCG CCG TCT TCC

181   Ala Lys Ser Arg Leu Gln Thr Ala Pro Val Pro Met Pro Asp Leu Lys Asn Val Lys Ser Lys Ile Gly Ser Thr Glu Asn Leu Lys His
541   GCC AAG AGC CGC CTG CAG ACA GCC CCC GTG CCC ATG CCA GAC CTG AAG AAT GTC AAG TCC AAG ATC GGC TCC ACT GAG AAC CTG AAG CAC

211   Gln Pro Gly Gly Gly Lys Val Gln Ile Val Tyr Lys Pro Val Asp Leu Ser Lys Val Thr Ser Lys Cys Gly Ser Leu Gly Asn Ile His
631   CAG CCG GGA GGC GGG AAG GTG CAA ATA GTC TAC AAA CCA GTT GAC CTG AGC AAG GTC ACC TCC AAG TGT GGC TCA TTA GGC AAC ATC CAT
```

FIG. 1A

```
241  His Lys Pro Gly Gly Gly Val Glu Gln Val Lys Ser Glu Lys Leu Asp Phe Lys Asp Arg Val Gln Ser Lys Ile Gly Ser Leu Asp Asn
721  CAT AAA CCA GGA GGT GGC CAG GTG GAA GTA AAA TCT GAG AAG CTT GAC TTC AAG GAC AGA GTC CAG TCG AAG ATT GGG TCC CTG GAC AAT

271  Ile Thr His Val Pro Gly Gly Gly Asn Lys Lys Ile Glu Thr His Lys Leu Thr Phe Arg Glu Asn Ala Lys Ala Lys Thr Asp His Gly
811  ATC ACC CAC GTC CCT GGC GGA GGA AAT AAG AAA ATT GAA ACC CAC AAG CTG ACC TTC CGG GAG AAC GCC AAA GCC AAG ACA GAC CAC GGG

301  Ala Glu Ile Val Tyr Lys Ser Pro Val Val Ser Gly Asp Thr Ser Pro Arg His Leu Ser Asn Val Ser Ser Thr Gly Ser Ile Asp Met
901  GCG GAG ATC GTG TAC AAG TCG CCA GTG GTG TCT GGG GAC ACG TCT CCA CGG CAT CTC AGC AAT GTC TCC AGC ACC GGC AGC ATC GAC ATG

331  Val Asp Ser Pro Gln Leu Ala Thr Leu Ala Asp Glu Val Ser Ala Ser Leu Ala Lys Gln Gly Leu ***
991  GTA GAC TCG CCC CAG CTC GCC ACG CTA GCT GAC GAG GTG TCT GCC TCC CTG GCC AAG CAG GGT TTG TGA TCAGGCCCCTGG
```

FIG.1B

SEQUENCE LISTING ( 1 ) GENERAL INFORMATION:

5,492,812

-continued ( i i i ) NUMBER OF SEQUENCES: 2

( 2 ) INFORMATION FOR SEQ ID NO:1:

( i ) SEQUENCE CHARACTERISTICS:
( A ) LENGTH: 1107 base pairs
( B ) TYPE: nucleic acid
( C ) STRANDEDNESS: single
( D ) TOPOLOGY: linear ( i i ) MOLECULE TYPE: DNA (genomic)

( i x ) FEATURE:
( A ) NAME/KEY: CDS
( B ) LOCATION: 38..1092

( x i ) SEQUENCE DESCRIPTION: SEQ ID NO:1:

```
CCGCCTCTGT CGACTATCAG GTGAACTTTG AACCAGG ATG GCT GAG CCC CGC CAG       55
                                        Met Ala Glu Pro Arg Gln
                                         1               5

GAG TTC GAA GTG ATG GAA GAT CAC GCT GGG ACG TAC GGG TTG GGG GAC       103
Glu Phe Glu Val Met Glu Asp His Ala Gly Thr Tyr Gly Leu Gly Asp
              10              15                  20

AGG AAA GAT CAG GGG GGC TAC ACC ATG CAC CAA GAC CAA GAG GGT GAC       151
Arg Lys Asp Gln Gly Gly Tyr Thr Met His Gln Asp Gln Glu Gly Asp
         25                  30                  35

ACG GAC GCT GGC CTG AAA GCT GAA GAA GCA GGC ATT GGA GAC ACC CCC       199
Thr Asp Ala Gly Leu Lys Ala Glu Glu Ala Gly Ile Gly Asp Thr Pro
     40                  45                  50

AGC CTG GAA GAC GAA GCT GCT GGT CAC GTG ACC CAA GCT CGC ATG GTC       247
Ser Leu Glu Asp Glu Ala Ala Gly His Val Thr Gln Ala Arg Met Val
 55                  60                  65                  70

AGT AAA AGC AAA GAC GGG ACT GGA AGC GAT GAC AAA AAA GCC AAG GGG       295
Ser Lys Ser Lys Asp Gly Thr Gly Ser Asp Asp Lys Lys Ala Lys Gly
                     75                  80                  85

GCT GAT GGT AAA ACG AAG ATC GCC ACA CCG CGG GGA GCA GCC CCT CCA       343
Ala Asp Gly Lys Thr Lys Ile Ala Thr Pro Arg Gly Ala Ala Pro Pro
             90                  95                  100

GGC CAG AAG GGC CAG GCC AAC GCC ACC AGG ATT CCA GCA AAA ACC CCG       391
Gly Gln Lys Gly Gln Ala Asn Ala Thr Arg Ile Pro Ala Lys Thr Pro
        105                  110                  115

CCC GCT CCA AAG ACA CCA CCC AGC TCT GGT GAA CCT CCA AAA TCA GGG       439
Pro Ala Pro Lys Thr Pro Pro Ser Ser Gly Glu Pro Pro Lys Ser Gly
    120                  125                  130

GAT CGC AGC GGC TAC AGC AGC CCC GGC TCC CCA GGC ACT CCC GGC AGC       487
Asp Arg Ser Gly Tyr Ser Ser Pro Gly Ser Pro Gly Thr Pro Gly Ser
135                  140                  145                  150

CGC TCC CGC ACC CCG TCC CTT CCA ACC CCA CCC ACC CGG GAG CCC AAG       535
Arg Ser Arg Thr Pro Ser Leu Pro Thr Pro Pro Thr Arg Glu Pro Lys
                155                  160                  165

AAG GTG GCA GTG GTC CGT ACT CCA CCC AAG TCG CCG TCT TCC GCC AAG       583
Lys Val Ala Val Val Arg Thr Pro Pro Lys Ser Pro Ser Ser Ala Lys
            170                  175                  180

AGC CGC CTG CAG ACA GCC CCC GTG CCC ATG CCA GAC CTG AAG AAT GTC       631
Ser Arg Leu Gln Thr Ala Pro Val Pro Met Pro Asp Leu Lys Asn Val
        185                  190                  195

AAG TCC AAG ATC GGC TCC ACT GAG AAC CTG AAG CAC CAG CCG GGA GGC       679
Lys Ser Lys Ile Gly Ser Thr Glu Asn Leu Lys His Gln Pro Gly Gly
    200                  205                  210

GGG AAG GTG CAA ATA GTC TAC AAA CCA GTT GAC CTG AGC AAG GTG ACC       727
Gly Lys Val Gln Ile Val Tyr Lys Pro Val Asp Leu Ser Lys Val Thr
215                  220                  225                  230

TCC AAG TGT GGC TCA TTA GGC AAC ATC CAT CAT AAA CCA GGA GGT GGC       775
```

```
Ser Lys Cys Gly Ser Leu Gly Asn Ile His His Lys Pro Gly Gly Gly
                235                     240                 245

CAG GTG GAA GTA AAA TCT GAG AAG CTT GAC TTC AAG GAC AGA GTC CAG          823
Gln Val Glu Val Lys Ser Glu Lys Leu Asp Phe Lys Asp Arg Val Gln
            250                     255                 260

TCG AAG ATT GGG TCC CTG GAC AAT ATC ACC CAC GTC CCT GGC GGA GGA          871
Ser Lys Ile Gly Ser Leu Asp Asn Ile Thr His Val Pro Gly Gly Gly
                265                     270                 275

AAT AAA AAG ATT GAA ACC CAC AAG CTG ACC TTC CGC GAG AAC GCC AAA          919
Asn Lys Lys Ile Glu Thr His Lys Leu Thr Phe Arg Glu Asn Ala Lys
            280                     285                 290

GCC AAG ACA GAC CAC GGG GCG GAG ATC GTG TAC AAG TCG CCA GTG GTG          967
Ala Lys Thr Asp His Gly Ala Glu Ile Val Tyr Lys Ser Pro Val Val
295                     300                     305             310

TCT GGG GAC ACG TCT CCA CGG CAT CTC AGC AAT GTC TCC TCC ACC GGC         1015
Ser Gly Asp Thr Ser Pro Arg His Leu Ser Asn Val Ser Ser Thr Gly
                315                     320                 325

AGC ATC GAC ATG GTA GAC TCG CCC CAG CTC GCC ACG CTA GCT GAC GAG         1063
Ser Ile Asp Met Val Asp Ser Pro Gln Leu Ala Thr Leu Ala Asp Glu
            330                     335                 340

GTG TCT GCC TCC CTG GCC AAG CAG GGT TG TGATCAGGCC CCTGG                 1107
Val Ser Ala Ser Leu Ala Lys Gln Gly
            345                 350
```

(2) INFORMATION FOR SEQ ID NO:2:

(i) SEQUENCE CHARACTERISTICS:
        (A) LENGTH: 351 amino acids
        (B) TYPE: amino acid
        (D) TOPOLOGY: linear (ii) MOLECULE TYPE: protein (xi) SEQUENCE DESCRIPTION: SEQ ID NO:2:

```
Met Ala Glu Pro Arg Gln Glu Phe Glu Val Met Glu Asp His Ala Gly
 1               5                  10                  15

Thr Tyr Gly Leu Gly Asp Arg Lys Asp Gln Gly Gly Tyr Thr Met His
             20                  25                  30

Gln Asp Gln Glu Gly Asp Thr Asp Ala Gly Leu Lys Ala Glu Glu Ala
         35                  40                  45

Gly Ile Gly Asp Thr Pro Ser Leu Glu Asp Glu Ala Ala Gly His Val
     50                  55                  60

Thr Gln Ala Arg Met Val Ser Lys Ser Lys Asp Gly Thr Gly Ser Asp
 65                  70                  75                  80

Asp Lys Lys Ala Lys Gly Ala Asp Gly Lys Thr Lys Ile Ala Thr Pro
                 85                  90                  95

Arg Gly Ala Ala Pro Pro Gly Gln Lys Gly Gln Ala Asn Ala Thr Arg
                100                 105                 110

Ile Pro Ala Lys Thr Pro Pro Ala Pro Lys Thr Pro Pro Ser Ser Gly
            115                 120                 125

Glu Pro Pro Lys Ser Gly Asp Arg Ser Gly Tyr Ser Ser Pro Gly Ser
        130                 135                 140

Pro Gly Thr Pro Gly Ser Arg Ser Arg Thr Pro Ser Leu Pro Thr Pro
145                 150                 155                 160

Pro Thr Arg Glu Pro Lys Lys Val Ala Val Val Arg Thr Pro Pro Lys
                165                 170                 175

Ser Pro Ser Ser Ala Lys Ser Arg Leu Gln Thr Ala Pro Val Pro Met
            180                 185                 190

Pro Asp Leu Lys Asn Val Lys Ser Lys Ile Gly Ser Thr Glu Asn Leu
```

|  | 195 |  |  |  |  | 200 |  |  |  |  | 205 |  |  |
|---|---|---|---|---|---|---|---|---|---|---|---|---|---|
| Lys | His 210 | Gln | Pro | Gly | Gly | Gly 215 | Lys | Val | Gln | Ile | Val 220 | Tyr | Lys | Pro | Val |
| Asp 225 | Leu | Ser | Lys | Val | Thr 230 | Ser | Lys | Cys | Gly | Ser 235 | Leu | Gly | Asn | Ile | His 240 |
| His | Lys | Pro | Gly | Gly 245 | Gly | Gln | Val | Glu | Val 250 | Lys | Ser | Glu | Lys | Leu 255 | Asp |
| Phe | Lys | Asp | Arg 260 | Val | Gln | Ser | Lys | Ile 265 | Gly | Ser | Leu | Asp | Asn 270 | Ile | Thr |
| His | Val | Pro 275 | Gly | Gly | Gly | Asn | Lys 280 | Lys | Ile | Glu | Thr | His 285 | Lys | Leu | Thr |
| Phe | Arg 290 | Glu | Asn | Ala | Lys | Ala 295 | Lys | Thr | Asp | His | Gly 300 | Ala | Glu | Ile | Val |
| Tyr 305 | Lys | Ser | Pro | Val | Val 310 | Ser | Gly | Asp | Thr | Ser 315 | Pro | Arg | His | Leu | Ser 320 |
| Asn | Val | Ser | Ser | Thr 325 | Gly | Ser | Ile | Asp | Met 330 | Val | Asp | Ser | Pro | Gln 335 | Leu |
| Ala | Thr | Leu | Ala 340 | Asp | Glu | Val | Ser | Ala 345 | Ser | Leu | Ala | Lys | Gln 350 | Gly |

DIAGNOSTIC METHOD FOR ALZHEIMER'S DISEASE BY SCREENING FOR TAU-PEPTIDES IN THE BLOOD OF A PATIENT

This is a continuation, of application Ser. No. 07/738,778, filed Aug. 1, 1991, now abandoned.

1. FIELD OF THE INVENTION

The present invention is directed to the diagnosis, subtyping and monitoring of Alzheimer's disease. Diagnostic methods and kits are described which utilize monoclonal antibodies, polyclonal antibodies or Fab fragments specific to peptide fragments of the tau family of proteins which are found in the blood or spinal fluid of individuals affected by Alzheimer's disease. Alternatively, tau-peptides can be used to detect circulating autoantibodies in such patients.

The diagnostic Alzheimer's disease detection kits of the present invention can be particularly useful in screening the overall population and identifying those individuals who have Alzheimer's disease as well as subtyping the affected individuals according to which member of the tau family of proteins they express.

2. BACKGROUND OF THE INVENTION

Alzheimer's disease is the most common form of both senile and presenile dementia in the world and is recognized clinically as relentlessly progressive dementia that presents with increasing loss of memory, intellectual function and disturbances in speech (Merritt, 1979, *A Textbook of Neurology*, 6th edition, pp. 484–489 Lea & Febiger, Philadelphia). The disease itself usually has a slow and insidious progress that affects both sexes equally, worldwide. It begins with mildly inappropriate behavior, uncritical statements, irritability, a tendency towards grandiosity, euphoria and deteriorating performance at work; it progresses through deterioration in operational judgement, loss of insight, depression and loss of recent memory; it ends in severe disorientation and confusion, apraxia of gait, generalized rigidity and incontinence (Gilroy & Meyer, 1979, *Medical Neurology*, pp. 175–179 MacMillan Publishing Co.). Alzheimer's disease afflicts an estimated 4 million human beings in the United States alone at a cost of 35 billion dollars a year (Hay & Ernst, 1987, *Am. J. Public Health*, 77:1169–1175). It is found in 10% of the population over the age of 65 and 47% of the population over the age of 85 (Evans et al., 1989, *JAMA*, 262:2551–2556). In addition, the disease is found at much lower levels in the younger age groups, usually beginning at about 30 years of age and even rarely in late childhood (Adams & Victor, 1977, *Principles of Neurology*, pp. 401–407).

The etiology of Alzheimer's disease is unknown. Evidence for a genetic contribution comes from several important observations such as the familial incidence, pedigree analysis, monozygotic and dizygotic twin studies and the association of the disease with Down's syndrome (for review see Baraitser, 1990, *The Genetics of Neurological Disorders*, 2nd edition, pp. 85–88). Nevertheless, this evidence is far from definitive and it is clear that one or more other factors are also required. Elevated concentrations of aluminum have been found in the brains of some patients dying with Alzheimer's disease (Crapper et al., 1976, *Brain*, 99:67–80) and one case report has documented markedly elevated levels of manganese in the tissues of a patient with Alzheimer's disease (Banta & Markesberg, 1977, *Neurology*, 27:213–216), which has led to the suggestion that high levels of these metals may be neurotoxic and lead to the development of Alzheimer's disease. It was interesting that the aluminum ions were found to be associated mainly with the nuclear chromatin in brain regions most likely to display neurofibrillary tangles in Alzheimer's disease. However, from a statistical point of view the absolute differences found for the aluminum levels between normal and Alzheimer brains were far from convincing. It has recently been suggested that defects in the transcriptional splicing of mRNA coding for the tau complex of microtubule associated proteins occur (for review see Kosik, 1990, *Curr. Opinion Cell Biol.*, 2:101–104) and/or that inappropriate phosphorylation of these proteins exists (Grundke-Igbak et al., 1986, *Proc. Natl. Acad. Sci. USA*, 83:4913–4917; Wolozin & Davies, 1987, *Ann. Neurol.* 22:521–526; Hyman et al., 1988, *Ann. Neurol.*, 23:371–379; Bancher et al., 1989, *Brain Res.*, 477:90–99). Furthermore, reduction in the enzymes involved in the synthesis of acetylcholine has led to the view of Alzheimer's disease as a cholinergic system failure (Danes & Moloney, 1976, *Lancet*, ii:1403–14). However, even if cholinergic neurons are most at risk in Alzheimer's disease, it appears likely that these reductions in enzyme activity are secondary to the degenerative process itself rather than causally related.

2.1 THE DIAGNOSIS OF ALZHEIMER'S DISEASE

The diagnosis of Alzheimer's disease at autopsy is somewhat time-consuming but is definitive. The gross pathological changes are found in the brain, which is underweight, and shows generalized atrophy of both the gray and white matter of the cerebral cortex, particularly in the temporal and frontal lobes, with widening of the sulci and narrowing of the gyri as well as compensatory symmetrical dilation of the third and lateral ventricles (Adams & Victor, 1977, *Principles of Neurology*, pp. 401–407; Merritt, 1979, *A Textbook of Neurology*, 6th edition, Lea & Febiger, Philadelphia, pp. 484–489). The histological changes in the brain are definitive. The most common lesion is the neurofibrillary tangle (Kidd, 1963, *Nature*, 197: 192–193; Kidd, 1964, Brain 87: 307–320), which consists of a tangled mass of paired helical filaments and occasional straight filaments located in the cytoplasm of affected neurons (Oyanagei, 1979, *Adv. Neurol. Sci.*, 18:77–88 (in Japanese) as quoted by Grundke-Iqbal et al., 1985, *Acta Neuropathol.*, 66:52–61). The other characteristic histological lesions are Hirano bodies within nerve cells of certain brain regions, neuritic dystrophy and amyloid angiopathy. In addition, there are prominent argentophilic senile neuritic plaques composed of enlarged, degenerating axonal endings, containing degraded cellular organelles and some paired helical filaments, that surround a core of mainly extracellular amyloid (Merritt, 1979, *A Textbook of Neurology*, 6th edition, Lea & Febiger, Philadelphia, pp. 484–489). Small amounts of these histological changes are found also in the brains of almost all very old humans at autopsy, even if they showed no symptoms of Alzheimer's disease before death (Tomlinson & Henderson, 1976, *Neurobiology of Aging*, p. 183, Terry & Gershon (eds.), Raven, N.Y.; Ball, 1976, *Neuropathol. Appl. Neurobiol.*, 2:395; Ball, 1977, *Acta Neuropathol.*, 37:111–118). However, the number and total amount of these histological changes in brain has been found to correlate well with the severity of the clinical signs and symptoms of Alzheimer's disease (Kidd, 1963, *Nature*, 197:192–193; Terry et al., 1964, *Am. J. Pathol.*, 44:269–297; Roth et al., 1966, *Nature*, 209:109–110; Blessed et al., 1968, *Br. J. Psychiat.*, 114:797–881; Tomlinson et al., 1970, *J. Neurol. Sci.*, 11: 205–242; Wisniewski, 1976, *J. Neurol. Sci.*, 27:173–181).

The diagnosis of Alzheimer's disease during life is more difficult than at autopsy since it depends upon an inexact clinical evaluation. In the middle stages and particularly in the earlier stages of the disease, the diagnosis is a matter of clinical judgement and success is markedly dependent upon the experience and clinical acumen of the attending physician or consultant. In the late stages of the disease however, clinical diagnosis is relatively straight-forward even if it is not completely unequivocal. In all cases, a wide variety of other diseases, presenting at least partially overlapping clinical pictures, must be positively ruled out before a diagnosis of Alzheimer's disease can be made. Usually a patient must be evaluated on a number of occasions over some period of time in order to document the deterioration in intellectual ability and other signs and symptoms before a diagnosis can be attempted with reasonable confidence. The necessity of repeated evaluation by a professional medical practitioner before a firm diagnosis can be made is costly, generates anxiety and can be frustrating to patients and their families. Furthermore, the development of an appropriate therapeutic strategy is greatly hampered by these difficulties in the objective and rapid diagnosis of the disease, particularly in the early stages where even a simple arrest of the progress of the disease would leave the patient with significant intellectual capacity and a reasonable quality of life.

No unequivocal laboratory test specific for Alzheimer's disease has been reported. European patent application No. 391714 discloses a method for the diagnosis of Alzheimer's disease based upon the detection of mature β-amyloid protein, its precursor protein or a fragment of β-amyloid protein in non-neural tissue biopsy using immunoassay techniques. However, this approach is non-specific since it has been recognized that a wide variety of degenerative diseases, lead to the production and deposition of β-amyloid protein in almost all human tissues. Furthermore, even though the gene coding for both the β-amyloid protein (Goldgaber et al., 1987, *Science*, 235:877–80; Tanzi et al., 1987a, *Science*, 235:880–884) and the gene for familial Alzheimer's disease (St. George-Hyslop et al., 1987, *Science*, 325:885–890) have been located on human chromosome 21, it has been shown that the linkage between the two genes is not very close (Van Broedkhoven et al., 1987, *Nature*, 329:153–155; Tanzi et al., 1987b, *Nature*, 329:156–157). In addition, it is known that despite some earlier claims, β-amyloid protein forms no part of the paired helical filaments within neurofibrillary tangles (for review see Wischik et al., 1989, *Curr. Opinion Cell Biol.*, 1:115–122). Therefore, even though β-amyloid protein is deposited in many tissues of patients with Alzheimer's disease, it has not been definitively linked to Alzheimer's disease in a manner different to its association with many other degenerative diseases. Thus, the diagnostic usefulness of antibodies directed to mature β-amyloid protein, its precursor or any of its fragments must be considered marginal at best.

2.2 NEUROFIBRILLARY TANGLES AND ALZHEIMER'S DISEASE

It is now known that the only definitive feature of Alzheimer's disease is the presence of grossly increased quantities of neurofibrillary tangles within the affected cortical regions of brain compared to either normal brain from humans of any age or to brain from any disease state other than Alzheimer's disease itself. However, the neurofibrillary tangles have not heretofore been exploited for use in a diagnostic or screening assay for Alzheimer's disease.

The progression of Alzheimer's disease is characterized by a loss of cortical substance in the brain. This fact has been well documented over many years by many different researchers. The most characteristic lesion in Alzheimer's disease is the presence of paired helical filaments in discrete, randomly interwoven groups or neurofibrillary tangles within affected cortical neurons. In addition, the number and size of these tangles within an affected neuron as well as the total number of tangles and the total amount of constituent tau-protein in an affected brain correlates with the progression and severity of the disease. Therefore, it is believed that as these tangles increase in size and number they must interfere with the physiological function of each cell in which they occur, eventually leading directly to the death and lysis of that cell. Recently, it has been reported that the cytosolic ATP-dependent protease signal protein, ubiquitin, becomes attached to neurofibrillary tangles (Mori et al., 1987, *Science*, 235:1641–1644). Since ubiquitinated proteins are rapidly degraded, this suggests that the affected cell recognizes the tangles as a foreign structure requiring degradation. It is further believed that this mechanism of cortical neuron death is responsible for the progressive loss of cortical substance and, therefore, the loss of intellectual capacity as well as the appearance of the other signs and symptoms of Alzheimer's disease.

The paired helical filaments are composed of an unknown protein of 90,000 molecular weight (Mr) associated with various tau-protein species. A tightly bound helical core is formed between the 90,000 Mr protein and the large middle domain of the tau-protein as well as a region of the C-terminal domain, which contains the imperfect tandem repeat. The structural conformation of the helical core allows the N-terminal and C-terminal domains of the tau-protein to protrude at some angle from the axis of the paired helical filament thereby forming a protease-sensitive coat around the paired helical filaments (Wischik et al., 1988, *Proc. Natl. Acad. Sci. USA.*, 85:4884–4888). The research groups working in this area are directing their efforts towards characterizing the protease-resistant core of the paired helical filaments in order to understand the nature of the stable interaction and the nature of the modification that occurs to tau-proteins in Alzheimer's disease (for reviews, see Wischik et al., 1989, *Curr. Opinion Cell Biol.*, 1:115–122; Kosik, 1990, *Curr. Opinion Cell Biol.*, 2:101–104). This orientation of research effort as well as research directed towards the molecular genetics of the tau-protein are likely to lead to an understanding of the primary cause of Alzheimer's disease.

From the foregoing, it is clear that no one concerned with Alzheimer's disease has realized that its diagnosis ultimately must depend upon the detection and quantitative measurement of the amount of the component substance or substances that constitute these neurofibrillary tangles in victims of the disease. The detection of associated substances that can also be found in other disease states can never be as definitive as the detection of the actual substance building up in affected neurons in Alzheimer's disease causing the eventual death of those cells. What has also not been realized is that the protease stability of the core of the paired helical filaments makes it unlikely that any part of the tau-protein or the 90,000 Mr protein present in this stable core will ever be found outside the brain. The slow destruction of these stable cores, following their release by dead neurons, can be conceived to occur only in situ and as a consequence of phagocytosis by microglia. The most likely reason for the reluctance or failure to recognize the potential of using components of the neurofibrillary tangles in the diagnosis of Alzheimer's disease relates to the natural abhorrence that a person would feel if required to biopsy the brain of any living human being even in the last stages of the disease in order to measure these substances. The biopsy procedure is extremely invasive and must leave the person so biopsied less than whole. However, the scientific community has not considered the possibility that biopsy might not be necessary in order to detect the substance or substances in question.

In contrast to the relevant literature, the diagnostic approach of the present invention is based on the recognition that the whole of the 200 amino acid N-terminal residues of the various tau-proteins as well as some portion of their 50 amino acid most C-terminal residues will be released when cleaved from the filaments by ubiquitin-recognizing proteases or other proteases during degeneration and rupture of affected neurons. The diagnostic assays of the invention are based on the principle that it is these cleaved latter segments of tau-proteins that can find their way into body fluids outside the brain and whose detection and quantitation are important for diagnostic purposes. Additional support for this last conclusion comes from the observation that other brain-specific, soluble and protease-sensitive proteins find their way into blood and spinal fluid following head trauma (Phillips et al., 1980, *Br. Med. J.*, 281:777–779; Brayne et al., 1982, *Lancet*, ii:1308–9) and various other types of neurological disorders (Thompson et al., 1980, *J. Neurol. Sci.*, 47:241–254; Willson et al., 1980, *Ann. Clin. Biochem.*, 17:110–113).

3. SUMMARY OF THE INVENTION

The present invention relates to methods and kits for diagnosing, subtyping and monitoring Alzheimer's disease. The invention is based, in part, on the discovery that proteolytic fragments of the amino and carboxy terminal amino acid residues of tau-proteins are released from the neurofibrillary tangles associated with the disease and can be detected in body fluids outside the brain.

The generation and purification of tau-proteins and peptide fragments of the amino terminal and carboxy terminal regions of tau-proteins are described. These tau-proteins and fragments thereof may be used to generate monoclonal antibodies, polyclonal antibodies or Fab fragments that, in turn, can be used in immunoassays to detect circulating tau-peptides in suspected individuals. Alternatively, the tau-peptides themselves may be used in immunoassays to detect circulating autoantibodies in such individuals.

3.1 DEFINITIONS

The term tau-protein is defined herein as any one of the proteins that comprise a single constituent part of the tau-complex of proteins.

The tau-complex of proteins is defined as that group of microtubule associated proteins (MAPS) from vertebrate brain that have the following characteristics: (a) co-purify with tubulin during the cycle purification of microtubules, particularly in the absence of glycerol (Asnes & Wilson, 1979, *Anal. Biochem.*, 98: 64–73; Murphy & Hiebsch, 1979, *Anal. Biochem.*, 96:225–235); (b) separate from tubulin present in the microtubules obtained by the cycle technique when an ice-cold sample of such a preparation is chromatographed on a phosphocellulose column, using 2-(N-morpholino)-ethanesulphonic acid (MES) buffer to remove tubulin and using MES buffer containing 1M NaCl to remove the tau-complex of proteins (Weingarten et al., 1975, *Proc. Natl. Acad. Sci. USA*, 72: 1858–1862; Cleveland et al., 1977, *J. Mol. Biol.*, 116:207–225.; Cleveland et al., 1979, *J. Biol. Chem.*, 254:12670–12678); (c) are included in a column of Sepharose 6B when chromatographed on such a matrix and where they migrate as an aggregated species not far from the exclusion volume but have individual unaggregated native molecular masses between 10,000 and 100,000 Mr regardless of axial ratio (Cleveland et al., 1977, *J. Mol. Biol.*, 116:207–225); (d) react with any of a number of antibodies described in the literature as "anti-tau" or with a commercial antibody described as anti-tau; (e) contain within each and every one of their C-terminal domains an imperfect tandem repeat of the type described in the literature (Lewis et al., 1988, *Science*, 242:936–939; Goedert et al., 1989, *EMBO J.*, 8:393–399; Kanai et al., 1989, J. Cell Biol., 109:1173–1184); and (f) are either heat-stable or heat-labile as described by Cleveland et al., 1977, *J. Mol. Biol.*, 116:207–225.

The term "forward sandwich assay" is defined in its most basic form as an assay wherein the sample to be tested containing the tau-peptide reacts with an anti-tau-peptide antibody that has been immobilzed upon a solid substrate; then a labeled second anti-tau-peptide antibody is added, which reacts with the tau-peptide at a different site.

The term "reverse sandwich assay" is defined in its most basic form as an assay wherein the labeled anti-tau-peptide antibody and sample to be tested containing the tau-peptide are first incubated together and then added to a second unlabeled anti-tau-peptide antibody that had previously been immobilized upon a solid substrate as in the "forward sandwich assay". Both the labeled and the unlabeled anti-tau-peptide must react with the tau-peptide at a different site.

4. DESCRIPTION OF THE FIGURE

FIG. 1 shows the complete nucleotide (SEQ ID NO: 1)and amino acid sequences (SEQ ID NO: 2) of one form of human tau-protein, reproduced from Goedert et al., 1988, *Proc. Natl. Acad. Sci. USA*, 85:4051–4055.

5. DETAILED DESCRIPTION OF THE INVENTION

The present invention results from the unexpected discovery of several physiological functions for individual proteins in the tau-complex of proteins that have not heretofore been described and are in addition to the well recognized function of promoting the polymerization of microtubules and/or their stability. This discovery has permitted the development of assays for the individual proteins in the tau-complex of proteins and their subsequent purification with retention of their native configuration and physiological activity. The invention is based, in part, on the discovery that in patients suffering from Alzheimer's disease there is proteolytic fragmentation of the tau-complex of proteins which occurs independently of phosphorylation, such that only the N-terminal domain comprising up to not more than the 200 most N-terminal amino acids or less and the C-terminal domain comprising up to only the 50 most C-terminal amino acids or less of tau will be released from the paired helical filaments, resident in the neurofibrillary tangle or free in the cytoplasm of affected neurons, and make their way into spinal fluid and blood.

This invention provides the first demonstration that any part of the tau-proteins of brain in victims of Alzheimer's disease are also present in body fluids outside the brain itself in concentrations greatly exceeding that found in normal humans that are not victims of Alzheimer's disease. This is achieved by examining a sample of body fluid, preferably blood or spinal fluid, and detecting the presence and quantity of any of the tau-proteins or fragments thereof. The detection and quantitative measurement of any of these tau-proteins or fragments thereof in body fluids in accordance with this invention is useful in confirming a clinical diagnosis of Alzheimer's disease in affected patients and in following the course of the disease. The invention is also useful in monitoring the disease during and subsequent to a period of treatment with agents that are being tested for their ability to stabilize, decrease or prevent the release of tau-proteins or fragments thereof from the brain.

Alternatively, the invention is directed to the production of tau-peptides for use in detecting circulating anti-tau-peptide autoantibodies in body fluids outside the brain in victims of Alzheimer's disease. The detection of circulating anti-tau-peptide autoantibodies in accordance with this invention is useful in confirming a clinical diagnosis of Alzheimer's disease in affected patients and in following the course of the disease.

For purposes of description only, the invention will be described in terms of: (a) generating tau-peptides; (b) generating antibodies that define the tau-peptide; and (c) diagnostic assays and kits for diagnosing subtyping or monitoring Alzheimer's disease.

5.1 PRODUCTION OF TAU-PEPTIDES

5.1.1 ENZYMATIC CLEAVAGE OF PURIFIED TAU-PROTEINS

The production of tau-peptides may be accomplished by isolating the paired helical filaments from human brains of patients who died with Alzheimers disease and purifying the helical complex containing the tau-protein and the 90,000 Mr protein (see Section 6, infra). The tau-protein is associated with the 90,000 Mr protein such that the 200 most amino terminal residues and the 50 most carboxy terminal residues protrude from the helical core of the complex thereby rendering those fragments susceptible to proteolytic enzymes.

The cleavage of the tau-protein into two large fragments of amino acid residues 1 to 151 and 154 to 352 and the dipeptide, Ser-Arg, may be accomplished using either one of the arginine-specific proteolytic enzymes such as thrombin (EC 3.4.13) as described recently (Joly et al., 1989, *J. Cell Biol.*, 109:2289–2294) or clostridiopeptidase B (clostripain) (EC 3.4.4.20). The preferred embodiment uses clostripain because the enzyme is a sulphydryl enzyme, requiring calcium ions for full activity. Consequently, its activity can be terminated conveniently by the addition of excess iodoacetamide and ethylene glycol-bis(β-aminoethyl ether) N,N, N', N'-tetraacetic acid (EGTA) In the case of either protease the concentration of tau-protein is adjusted to 100 µg/ml before beginning the digestion. Purified clostripain is used at a concentration of 4 international units/ml in the following buffer (50 mM phosphate buffer pH 7.7, 1 mM β-mercaptoethanol, and 1 mM calcium acetate). Soybean trypsin inhibitor (clostripain/inhibitor molar ratio=10/1) is added in order to eliminate any small residual trypsin activity in commercially available preparations of the enzyme. The cleavage reaction is conducted at 37° C. and is terminated by the addition of a sufficient volume of a 100 mM stock solution EGTA, pH 7.7, containing 100 mM iodoacetimide to give a final concentration of 2 mM EGTA in the protease reaction mixture. The exact time required for proteolysis varies with each tau-protein and markedly depends upon the batch of clostripain used. Therefore, the optimum time for a single cleavage must be determined for each combination of clostripain batch and tau-protein used. The time course of the cleavage reaction is determined by conducting the reaction as described above, but on a 20 µl volume and assaying the cleavage reaction by subjecting samples at various times to sodium dodecyl sulphate polyacrylamide gel electrophoresis (SDS PAGE) according to the method of Laemmli, (*Nature*, 1970, 227:680–684) as modified by Studier, *Sci.*, 176:367–376 (1972) using a 10% (w/v) polyacrylamide resolving gel followed by Serva blue staining and destaining in the usual manner of anyone familiar with the art.

The two large tau-peptide fragments resulting from either thrombin or clostripain proteolysis may be further cleaved by digestion with trypsin, which cleaves on the carboxy terminus of lysine or arginine residues. See for example, the techniques described in *Current Protocols in Molecular Biology*, Ausubel et al., Green Publish. Assoc. & Wiley Interscience, Ch. 10.

The sequence of tau-peptides derived from proteolytic digestion may be identified using the Edman degradation method of protein sequencing. This method sequentially removes one amino acid residue at a time from the amino terminal end of a peptide for subsequent sequence identification by chromatographic procedures. See for example, the techniques described in Konigsberg and Steinman, 1977, *Strategy and Methods of Sequence Analysis*, in Neurath and Hill (eds.), The Proteins (3rd ed.) Vol. 3, pp. 1–178, Academic Press. In addition, sequence analysis of tau-peptides may be accelerated by using an automated liquid phase amino acid sequenator following recently described techniques (Hewick et al., 1981, *J. Biol. Chem.*, 256:7990–7997; Stein and Undefriend, 1984, *Analy. Chem.*, 136:7–23), thereby allowing for the analysis of picomolar quantities of tau-peptides containing up to 50 amino acid residues in length.

5.1.2 CHEMICAL SYNTHESIS OF TAU-PEPTIDES

Tau-peptides can also be produced by chemical synthesis of the amino acid sequence of a tau-protein (Goedert et al., 1988, *Proc. Natl. Acad. Sci. USA*, 85:4051–4055), as predicted from the cloning and sequencing of a cDNA coding for a tau-protein. This tau-protein sequence information may be utilized to predict the appropriate amino and carboxy terminal tau-peptides to be chemically synthesized using standard peptide synthesis methods known in the art. These methods include a solid-phase method devised by R. Bruce Merrifield, (Erickson and Merrifield, "Solid-Phase Peptide Synthesis", in *The Proteins*, Volume 2, H. Neurath & R. Hill (eds.) Academic Press, Inc., New York pp. 255–257; Merrifield, 1986, "Solid phase synthesis", *Science*, 242:341–347). In the solid-phase method, amino acids are added stepwise to a growing peptide chain that is linked to an insoluble matrix, such as polystyrene beads. A major advantage of this method is that the desired product at each stage is bound to beads that can be rapidly filtered and washed and thus the need to purify intermediates is obviated. All of the reactions are carried out in a single vessel, which eliminates losses due to repeated transfers of products. This solid phase method of chemical peptide synthesis can readily be automated making it feasible to routinely synthesize peptides containing about 50 residues in good yield and purity (Stewart and Young, 1984, *Solid Phase Peptide Synthesis*, 2nd ed., Pierce Chemical Co.; Tam et al., 1983, *J. Am. Chem. Soc.*, 105:6442). For example, tau-peptides corresponding to amino acid residues 1 to 30 and 331 to 352 as depicted in FIG. 1 could be synthesized.

5.1.3 CLONING AND EXPRESSION OF RECOMBINANT

TAU-PROTEINS AND/OR TAU-PEPTIDES

The production of tau-peptides can further be achieved by recombinant DNA technology. For example, appropriate tau nucleotide coding sequences may be synthesized, cloned and expressed in appropriate host cells. Since the DNA sequence encoding for a tau-protein is known (Goeddert et al., 1988, *Proc. Natl. Acad. Sci., USA* 85:4051–4055), DNA probes may be synthesized by standard methods known in the art to screen cDNA libraries prepared from brain tissue of Alzheimer's disease patients for the specific tau-protein cDNA's. These DNA probes can further be used to isolate the entire family of tau-protein genes from these cDNA libraries using methods which are well known to those skilled in the art. See, for example, the techniques described in Maniatis et al., 1982, *Molecular Cloning A Laboratory Manual*, Cold Spring Harbor Laboratory, N.Y., Chapter 7.

The polymerase chain reaction (PCR) technique can be utilized to amplify the individual members of the tau family for subsequent cloning and expression of tau-protein cDNAs (e.g., see U.S. Pat. Nos. 4,683,202; 4,683,195; 4,889,818; Gyllensten et al., 1988, *Proc. Nat'l Acad. Sci. USA*, 85:7652–7656; Ochman et al., 1988, *Genetics*, 120:621–623; Triglia et al., 1988, *Nucl. Acids. Res.*, 16:8156; Frohman et al., 1988, *Proc. Nat'l Acad. Sci. USA*, 85:8998–9002; Loh et al., 1989, *Science*, 243:217–220).

Methods which are well known to those skilled in the art can be used to construct expression vectors containing tau-proteins or fragments thereof coding sequences and appropriate transcriptional/translational control signals. These methods include in vitro recombinant DNA techniques, synthetic techniques and in vivo recombination/genetic recombination. See, for example, the techniques described in Maniatis et al., 1982, Molecular Cloning A Laboratory Manual, Cold Spring Harbor Laboratory, N.Y., Chapter 12.

A variety of host-expression vector systems may be utilized to express tau-proteins or fragments thereof. These include but are not limited to microorganisms such as bacteria transformed with recombinant bacteriophage DNA, plasmid DNA or cosmid DNA expression vectors containing a coding sequence for a tau-protein or fragment thereof; yeast transformed with recombinant yeast expression vectors containing a coding sequence for a tau-protein or fragment thereof; insect cell systems infected with recombinant virus expression vectors (e.g., baculovirus) containing a coding sequence for a tau-protein or fragment thereof; or animal cell systems infected with recombinant virus expression vectors (e.g., adenovirus, vaccinia virus) containing a coding sequence for a tau-protein or fragment thereof.

The expression elements of these vectors vary in their strength and specificities. Depending on the host/vector system utilized, any of a number of suitable transcription and translation elements, including constitutive and inducible promoters, may be used in the expression vector. For example, when cloning in bacterial systems, inducible promoters such as pL of bacteriophage λ, plac, ptrp, ptac (ptrp-lac hybrid promoter) and the like may be used; when cloning in insect cell systems, promoters such as the baculovirus polyhedrin promoter may be used; when cloning in mammalian cell systems, promoters such as the adenovirus late promoter or the vaccinia virus 7.5K promoter may be used. Promoters produced by recombinant DNA or synthetic techniques may also be used to provide for transcription of the inserted coding sequence for a tau-protein or fragment thereof.

In yeast, a number of vectors containing constitutive or inducible promoters may be used. For a review see, Current Protocols in Molecular Biology, Vol. 2, 1988, Ed. Ausubel et al., Greene Publish. Assoc. & Wiley Interscience Ch. 13; Grant et al., 1987, Expression and Secretion Vectors for Yeast, in Methods in Enzymology, Eds. Wu & Grossman, 1987, Acad. Press, N.Y., Vol. 153, pp. 516–544; Glover, 1986, DNA Cloning, Vol. II, IRL Press, Wash., D.C. Ch.3; and Bitter, 1987, Heterologous Gene Expression in Yeast, Methods in Enzymology, Eds. Berger & Kimmel, Acad. Press, N.Y., Vol. 152, pp. 673–684; and The Molecular Biology of the Yeast Saccharomyces, 1982, Eds. Strathern et al., Cold Spring Harbor Press, Vols. I and II. For complementation assays in yeast, cDNAs for tau-proteins or fragments thereof may be cloned into yeast episomal plasmids (YEp) which replicate autonomously in yeast due to the presence of the yeast 2μ circle. The tau-protein or fragment thereof sequence may be cloned behind either a constitutive yeast promoter such as ADH or LEU2 or an inducible promoter such as GAL (Cloning in Yeast, Chpt. 3, R. Rothstein In; DNA Cloning Vol. 11, A Practical Approach, Ed. DM Glover, 1986, IRL Press, Wash., D.C.). Constructs may contain the 5' and 3' non-translated regions of a cognate tau-protein mRNA or those corresponding to a yeast gene. YEp plasmids transform at high efficiency and the plasmids are extremely stable. Alternatively vectors may be used which promote integration of foreign DNA sequences into the yeast chromosome.

A particularly good expression system which could be used to express tau-proteins or fragments thereof is an insect system. In one such system, *Autographa californica* nuclear polyhedrosis virus (AcNPV) is used as a vector to express foreign genes. The virus grows in *Spodoptera frugiperda* cells. The tau-protein or fragment thereof coding sequence may be cloned into non-essential regions (for example the polyhedrin gene) of the virus and placed under control of an AcNPV promoter (for example the polyhedrin promoter). Successful insertion of the polyhedrin gene results in production of non-occluded recombinant virus (i.e., virus lacking the proteinaceous coat coded for by the polyhedrin gene). These recombinant viruses are then used to infect *Spodoptera frugiperda* cells in which the inserted gene is expressed. (e.g., see Smith et al., 1983, *J. Biol.*, 46:586; Smith, U.S. Pat. No. 4,215,051).

In cases where an adenovirus is used as an expression vector, the tau-protein or fragment thereof coding sequence may be ligated to an adenovirus transcription/translation control complex, e.g., the late promoter and tripartite leader sequence. This chimeric gene may then be inserted in the adenovirus genome by in vivo or in vitro recombination. Insertion in a non-essential region of the viral genome (e.g., region E1 or E3) will result in a recombinant virus that is viable and capable of expressing the tau-protein of fragment thereof in infected hosts. (e.g., See Logan & Shenk, 1984, *Proc. Natl. Acad. Sci., (USA)* 81:3655–3659). Alternatively, the vaccinia 7.5K promoter may be used. (e.g., see Mackett et al., 1982, *Proc. Natl. Acad. Sci., (USA)* 79:7415–7419; Mackett et al., 1984, *J. Virol.*, 49:857–864; Panicali et al., 1982, *Proc. Natl. Acad. Sci.*, 79: 4927–4931).

Specific initiation signals may also be required for efficient translation of the inserted tau-protein or fragment thereof coding sequences. These signals include the ATG initiation codon and adjacent sequences. In cases where the entire tau-protein genome, including its own initiation codon and adjacent sequences, are inserted into the appropriate expression vectors, no additional translational control signals may be needed. However, in cases where only a portion of the tau-protein coding sequence is inserted, exogenous translational control signals, including the ATG initiation codon, must be provided. Furthermore, the initiation codon must be in phase with the reading frame of the tau-protein or fragment thereof coding sequence to ensure translation of the entire insert. These exogenous translational control signals and initiation codons can be of a variety of origins, both natural and synthetic. The efficiency of expression may be enhanced by the inclusion of appropriate transcription enhancer elements, transcription terminators, etc. (see Bitter et al., 1987, *Methods in Enzymol.*, 153:516–544).

In addition, a host cell strain may be chosen which modulates the expression of the inserted sequences, or modifies and processes the gene product in the specific fashion desired. Expression driven by certain promoters can be elevated in the presence of certain inducers, (e.g., zinc and cadmium ions for metallothionein promoters). Therefore, expression of the genetically engineered tau-protein or fragment thereof may be controlled. This is important if the protein product of the cloned foreign gene is lethal to host cells. Furthermore, modifications (e.g., glycosylation) and processing (e.g., cleavage) of protein products may be important for the function of the protein. Different host cells have characteristic and specific mechanisms for the post-translational processing and modification of proteins. Appropriate cell lines or host systems can be chosen to ensure the correct modification and processing of the foreign protein expressed.

The host cells which contain the tau-protein or fragment thereof coding sequence and which express the biologically active tau-protein or fragment thereof gene product may be identified by at least four general approaches: (a) DNA-DNA hybridization; (b) the presence or absence of "marker" gene functions; (c) assessing the level of transcription as measured by expression of tau-protein mRNA transcripts in host cells; and (d) detection of tau-protein gene products as measured by immunoassays or by its biological activity.

In the first approach, the presence of the tau-protein or fragment thereof coding sequence inserted in the expression vector can be detected by DNA-DNA hybridization using probes comprising nucleotide sequences that are homologous to the tau-protein coding sequence or particular portions thereof substantially as described recently (Goeddert et al., 1988, *Proc. Natl. Acad. Sci. USA*, 85:4051–4055).

In the second approach, the recombinant expression vector/host system can be identified and selected based upon the presence or absence of certain "marker" gene functions (e.g., thymidine kinase activity, resistance to antibiotics, resistance to methotrexate, transformation phenotype, occlusion body formation in baculovirus, etc.). For example, if the tau-protein or fragment thereof coding sequence is inserted within a marker gene sequence of the vector, recombinants containing the tau-protein or fragment thereof coding sequence can be identified by the absence of the marker gene function. Alternatively, a marker gene can be placed in tandem with the tau-protein or fragment thereof coding sequence under the control of the same or different promoter used to control the expression of the tau coding sequence. Expression of the marker in response to induction or selection indicates expression of the tau-protein coding sequence.

In the third approach, transcriptional activity for the tau-protein or fragment thereof coding region can be assessed by hybridization assays. For example, RNA can be isolated and analyzed by Northern blot using a probe homologous to the tau-protein or fragment thereof coding sequence or particular portions thereof substantially as described (Goeddert et al., 1988, *Proc. Natl. Acad. Sci. USA*, 85:4051–4055). Alternatively, total nucleic acids of the host cell may be extracted and assayed for hybridization to such probes.

In the fourth approach, the expression of the tau-protein or fragment thereof product can be assessed immunologically, for example by Western blots, immunoassays such as radioimmunoprecipitation, enzyme-linked immunoassays and the like.

Once a recombinant that expresses a tau-protein or fragment thereof is identified, the gene product should be analyzed. This can be achieved by assays based on the physical, immunological or functional properties of the product.

A tau-protein or fragment thereof should be immunoreactive whether it results from the expression of the entire gene sequence, a portion of the gene sequence or from two or more gene sequences which are ligated to direct the production of chimeric proteins. This reactivity may be demonstrated by standard immunological techniques, such as radioimmunoprecipitation, radioimmune competition, or immunoblots.

5.2 GENERATION OF ANTIBODIES THAT DEFINE TAU-PEPTIDES

Various procedures known in the art may be used for the production of antibodies to epitopes of the tau-protein. Such antibodies include but are not limited to polyclonal, monoclonal, chimeric, single chain, Fab fragments and an Fab expression library. For the production of antibodies, various host animals may be immunized by injection with a particular tau-protein, or a synthetic tau-peptide, including but not limited to rabbits, mice, rats, etc. Various adjuvants may be used to increase the immunological response, depending on the host species, including but not limited to Freund's (complete and incomplete), mineral gels such as aluminum hydroxide, surface active substances such as lysolecithin, pluronic polyols, polyanions, peptides, oil emulsions, keyhole limpet hemocyanin, dinitrophenol, and potentially useful human adjuvants such as BCG (bacille Calmette-Guerin) and corynebacterium parvum.

Monoclonal antibodies to peptides of tau may be prepared by using any technique which provides for the production of antibody molecules by continuous cell lines in culture. These include but are not limited to the hybridoma technique originally described by Kohler and Milstein, (*Nature*, 1975, 256:495–497), the more recent human B-cell hybridoma technique (Kosbor et al., 1983, *Immunology Today*, 4:72) and the EBV-hybridoma technique (Cole et al., 1985, *Monoclonal Antibodies and Cancer Therapy*, Alan R. Liss, Inc., pp. 77–96). In an additional embodiment of the invention monoclonal antibodies specific to tau-peptides may be produced in germ-free animals utilizing recent technology (PCT/US90/02545). According to the invention, human antibodies may be used and can be obtained by using human hybridomas (Cote at al., 1983, *Proc. Natl. Acad. Sci.*, 80:2026–2030) or by transforming human B cells with EBV virus in vitro (Cole et al., 1985, in, *Monoclonal Antibodies and Cancer Therapy*, Alan R. Liss, pp. 77–96). In fact, according to the invention, techniques developed for the production of "chimeric antibodies" (Morrison et al., 1984, *Proc. Natl. Acad. Sci.*, 8 1:6851–6855; Neuberger et al., 1984, *Nature*, 312:604–608; Takeda et al., 1985, *Nature*, 314:452–454) by splicing the genes from a mouse antibody molecule of appropriate antigen specificity together with genes from a human antibody molecule of appropriate biological activity can be used; such antibodies are within the scope of this invention.

According to the invention, techniques described for the production of single chain antibodies (U.S. Pat. No. 4,946,778) can be adapted to produce tau-peptide-specific single chain antibodies.

An additional embodiment of the invention utilizes the techniques described for the construction of Fab expression libraries (Huse et al., 1989, *Science*, 246:1275–1281) to allow rapid and easy identification of monoclonal Fab fragments with the desired specificity to tau-peptides.

Antibody fragments which contain specific binding sites of tau-peptides may be generated by known techniques. For example, such fragments include but are not limited to: the $F(ab')_2$ fragments which can be produced by pepsin digestion of the antibody molecule and the Fab fragments which can be generated by reducing the disulfide bridges of the $F(ab')_2$ fragments.

5.3 DIAGNOSTIC ASSAYS AND KITS FOR ALZHEIMER'S DISEASE

Yet another purpose of the present invention is to provide reagents for use in diagnostic assays for the detection of tau-peptides from individuals suffering from Alzheimer's disease.

In one mode of this embodiment, tau-peptides of the present invention may be used as antigens in immunoassays for the detection of those individuals suffering from Alzheimer's disease. The proteins, polypeptides and peptides of the present invention may be used in any immunoassay system known in the art including, but not limited to: radioimmunoassays, enzyme-linked immunosorbent assay, "sandwich" assays, precipitin reactions, gel diffusion immunodiffusion assays, agglutination assays, fluorescent immunoassays, protein A immunoassays and immunoelectrophoresis assays, to name but a few. U.S. Pat. No. 4,629,783 and patents cited therein also describe suitable assays.

According to the present invention, monoclonal or polyclonal antibodies produced to various forms of the tau-protein, can be used in an immunoassay on samples of blood, spinal fluid or other body fluid to diagnose patients with Alzheimer's disease.

In practicing the invention, a sample of blood is removed from the patient by venesection and placed in contact with an anticoagulant such as EDTA, mixed, centrifuged at 600 g for 10 min and the plasma removed as is common in the art or a sample of spinal fluid is removed from the patient by lumbar puncture.

The antibodies described in Section 5.2 supra may be used as the basic reagents in a number of different immunoassays to determine the presence of a particular tau-peptide in a sample of blood or spinal fluid. Generally speaking, the antibodies can be employed in any type of immunoassay, whether qualitative or quantitative. This includes both the two-site sandwich assay and the single site immunoassay of the non-competitive type, as well as in traditional competitive binding assays.

Particularly preferred, for ease of detection, and its quantitative nature, is the sandwich or double antibody assay, of which a number of variations exist, all of which are intended to be encompassed by the present invention.

For example, in a typical forward sandwich assay, unlabeled antibody is immobilized on a solid substrate, e.g., microtiter plate wells, and the sample to be tested is brought into contact with the bound molecule. After a suitable period of incubation, for a period of time sufficient to allow formation of an antibody-antigen binary complex, a second antibody, labelled with a reporter molecule capable of inducing a detectable signal, is then added and incubation is continued allowing sufficient time for binding with the antigen at a different site and the formation of a ternary complex of antibody-antigen-labeled antibody. Any unreacted material is washed away, and the presence of the antigen is determined by observation of a signal, which may be quantitated by comparison with a control sample containing known amounts of antigen. Variations on the forward sandwich assay include the simultaneous assay, in which both sample and antibody are added simultaneously to the bound antibody, or a reverse sandwich assay in which the labelled antibody and sample to be tested are first combined, incubated and added to the unlabelled surface bound antibody. These techniques are well known to those skilled in the art, and the possibility of minor variations will be readily apparent. As used herein, "sandwich assay" is intended to encompass all variations on the basic two-site technique.

For the sandwich assays of the present invention, the only limiting factor is that both antibodies have different binding specificities for the tau-peptide. Thus, a number of possible combinations are possible.

As a more specific example, in a typical forward sandwich assay, a primary antibody is either covalently or passively bound to a solid support. The solid surface is usually glass or a polymer, the most commonly used polymers being cellulose, polyacrylamide, nylon, polystyrene, polyvinylchloride or polypropylene. The solid supports may be in the form of tubes, beads, discs or microplates, or any other surfaces suitable for conducting an immunoassay. The binding processes are well known in the art. Following binding, the solid phase-antibody complex is washed in preparation for the test sample. An aliquot of the body fluid containing the tau-peptide to be tested is then added to the solid phase complex and incubated at 25° C. for a period of time sufficient to allow binding of any tau-peptide present to the antibody specific for tau-peptide. The second antibody is then added to the solid phase complex and incubated at 25° C. for an additional period of time sufficient to allow the second antibody to bind to the primary antibody-antigen solid phase complex. The second antibody is linked to a reporter molecule, the visible signal of which is used to indicate the binding of the second antibody to any antigen in the sample. By "reporter molecule", as used in the present specification is meant a molecule which by its chemical nature, provides an analytically detectable signal which allows the detection of antigen-bound antibody. Detection must be at least relatively quantifiable, to allow determination of the amount of antigen in the sample, this may be calculated in absolute terms, or may be done in comparison with a standard (or series of standards) containing a known normal level of antigen.

The most commonly used reporter molecules in this type of assay are either enzymes or fluorophores. In the case of an enzyme immunoassay an enzyme is conjugated to the second antibody, often by means of glutaraldehyde or periodate. As will be readily recognized, however, a wide variety of different conjugation techniques exist, which are well known to the skilled artisan. Commonly used enzymes include horseradish peroxidase, glucose oxidase, β-galactosidase and alkaline phosphatase, among others. The substrates to be used with the specific enzymes are generally chosen for the production, upon hydrolysis by the corresponding enzyme, of a detectable color change. For example, p-nitrophenyl phosphate is suitable for use with alkaline phosphatase conjugates; for peroxidase conjugates, 1,2-phenylenediamine or toluidine are commonly used. It is also possible to employ fluorogenic substrates, which yield a fluorescent product rather than the chromogenic substrates noted above. In all cases, the enzyme-labelled antibody is added to the first antibody-tau-peptide complex and allowed to bind to the complex, then the excess reagent is washed away. A solution containing the appropriate substrate is then added to the tertiary complex of antibody-antigen-labeled antibody. The substrate reacts with the enzyme linked to the second antibody, giving a qualitative visual signal, which may be further quantitated, usually spectrophotometrically, to give an evaluation of the amount of antigen which is present in the serum sample.

Alternately, fluorescent compounds, such as fluorescein or rhodamine, may be chemically coupled to antibodies without altering their binding capacity. When activated by illumination with light of a particular wavelength, the fluorochrome-labelled antibody absorbs the light energy, inducing a state of excitability in the molecule, followed by emission of the light at a characteristic longer wavelength. The emission appears as a characteristic color visually detectable with a light microscope. As in the enzyme immunoassay (EIA), the fluorescent-labelled antibody is allowed to bind to the first antibody-tau-peptide complex. After washing the unbound reagent, the remaining ternary complex is then exposed to light of the appropriate wavelength, and the fluorescence observed indicates the presence of the antigen. Immunofluorescence and EIA techniques are both very well established in the art and are particularly preferred for the present method. However, other reporter molecules, such as radioisotopes, chemiluminescent or bioluminescent molecules may also be employed. It will be readily apparent to the skilled artisan how to vary the procedure to suit the required use.

Alternatively, the sample to be tested either human blood or spinal fluid containing the tau-peptide may be used in a single site immunoassay wherein it is adhered to a solid substrate either covalently or noncovalently. An unlabeled anti-tau-peptide antibody is brought into contact with the sample bound on the solid substrate. After a suitable period of incubation, for a period of time sufficient to allow formation of an antibody-antigen binary complex a second antibody, labelled with a reporter molecule capable of inducing a detectable signal, is then added and incubation is continued allowing sufficient time for the formation of a ternary complex of antigen-antibody-labeled antibody. For the single site immunassay, the second antibody may be a general antibody (i.e., zenogeneic antibody to immunoglobulin, particularly anti-(IgM and IgG) linked to a reporter molecule) that is capable of binding an antibody that is specific for the tau-peptide of interest.

Alternatively, the purified tau-proteins or fragments thereof, described in Section 5.1, supra, may be used in a diagnostic assay to detect circulating anti-tau-peptide autoantibodies wherein they are adhered to a solid support either covalently or non-covalently. The sample, either human blood or spinal fluid diluted in an appropriately buffered medium, is added to the solid support and a sufficient time is allowed for complex formation between the tau-proteins or fragments thereof and any cognate autoantibodies in the sample. The supernatant is removed and the solid support is washed to remove any non-specifically bound proteins. To the complex may be added xenogeneic antisera to human immunoglobulin, particularly anti-(human Ig M and Ig G) in an appropriately buffered medium. The xenogeneic antisera will normally be labeled with a reporter molecule as described above for the forward sandwich assay. Instead of xenogeneic antisera, proteins specific for the immune complex may be employed, e.g., *S. aureus* protein A. The label may then be detected as described above for the forward sandwich assay.

6. EXAMPLE: PRODUCTION AND PURIFICATION OF IMMUNOGENS FOR ANTIBODY PRODUCTION

6.1. PURIFICATION OF MICROTUBULES FROM BOVINE BRAIN BY THE CYCLE PROCEDURE AS A SOURCE OF NATIVE, PHYSIOLOGICALLY ACTIVE MICROTUBULE ASSOCIATED PROTEINS

The cycle purification of microtubules from bovine brain was performed in the presence of guanosine triphosphate and low concentrations of magnesium ions in order to obtain high ratios of microtubule associated proteins to tubulin. This cycle-purification was carried out in five separate steps according to a modification of the method described by Asnes & Wilson, (1979, *Anal. Biochem.*, 98: 64–73).

Step (1) Transport & Dissection: Eight bovine brains (approximately 350 gram (g) each) were removed, cut into pieces, placed in ice-cold transport buffer [20 mM phosphoric acid (adjusted to pH 6.75 with 2M NaOH) 100 mM sodium glutamate, 300 mM sucrose] containing ice cubes made from transport buffer and transported in an ice bucket from the abattoir to the laboratory. The meninges, superficial blood vessels and the majority of the white matter was removed and discarded. The remaining brain tissue (approximately 1200 g) was drained and weighed.

Step (2) Homogenization: The selected brain tissue was dispersed using two separate maneuvers sequentially. The weighed brain tissue from step (1) was passed once through a domestic electric mincer and added to homogenization buffer [200 mM phosphoric acid (adjusted to pH 6.75 with 2M NaOH), 100 mM sodium glutamate, 300 mM sucrose, 4 mM β-mercaptoethanol, 0.3 mM phenylmethanesulphonylfluoride (PMSF) (stock solution, 100 mM in dimethylformamide (DMF)), 0.3 mM Nα-p-tosyl-1-lysine chloromethylketone (TLCK) (prepared in PMSF stock solution), 50 μg/ml leupeptin, few crystals of catalase] (at 0° C. and at a concentration of 1.5 ml buffer/g tissue). The material was dispersed by gentle stirring with a glass rod. The resulting suspension was then homogenized in three batches with two complete strokes (up and down twice for each batch separately) of a motor driven 1 liter (L) glass (2.2 inch diameter× 18 inch long) Potter—Elvehjem homogenizer fitted with a 2 inch long teflon pestle (0.005 inch clearance) at 0° C.

Step (3) First Cycle: Approximately 3000 ml of the homogenate was added to twelve 250 ml plastic centrifuge tubes and centrifuged at 27,880 g (13,000 rpm in two Sorval RC5B preparative centrifuges containing two GSA rotors precooled to 3° C.) for 53 minutes at 0°–4° C. The supernatants were carefully removed, combined and cofactor buffer [2.5 mM GTP, .50 mM $MgCl_2$, 1.0 mM EGTA (10×stock solution adjusted to pH 6.75 at 0° C. with NaOH)] prepared in homogenization buffer was added. The solution was mixed and then approximately 1L portions together with a glass thermometer was placed in separate polyethene sleeves (10 inch×14 inch) and heat sealed. The loaded sleeves were gently agitated in a 50° C. water bath until the temperature of their contents reached 30° C. whereupon they were immediately transferred to a 30° C. water bath where the incubation continued without further agitation for the remainder of a total period of 30 minutes. Assembly was followed viscometrically using calibrated 100-size Cannon Ubbleohde glass viscometers. Approximately 2400 ml of the assembled extract was transferred to 12 clean 250 ml plastic centrifuge jars and centrifuged at 27,880 g (13,000 rpm in two Sorval RC5B preparative centrifuges containing two Sorval GSA rotors prewarmed to 30° C.) for 42 minutes at 30° C. The supernatant was carefully removed with an aspirator and its volume was measured, recorded and discarded.

Step (4) Second Cycle: The final pellet from the first cycle was resuspended in ice-cold homogenization buffer without sucrose (10% of volume of the supernatant from the first cycle) using a precooled small Dounce homogenizer. Approximately 220 ml of the resuspended pellet was incubated at 0° C. for 30 minutes, added to six 36 ml plastic centrifuge tubes, and centrifuged at 39,000 g (14,627 rpm in a Sorval OTD centrifuge containing a Sorval AH-627 rotor precooled to 3° C.) for 40 minutes at 0° to 4° C. The supernatant was carefully transferred to a 1 L glass conical flask and cofactor buffer was added. The solution was mixed and gently swirled in the 50° C. water bath until the temperature reached 30° C. The flask was then immediately transferred to a 30° C. water bath where the incubation continued without further agitation for a total period of only 10 minutes. The extract was transferred to six 36 ml plastic centrifuge tubes and centrifuged at 39,000 g (14,726 rpm in a Sorval OTD ultracentrifuge containing a Sorval AH-627 rotor) for 30 minutes at 30° C. The supernatant was removed carefully with an aspirator and its volume was measured and discarded.

Step (5) Third Cycle—The final pellet from the second cycle was resuspended in ice-cold homogenization buffer without sucrose (40% of the volume of the supernatant from the second cycle) using a clean precooled small Dounce homogenizer. Approximately 90 ml of resuspended pellet was incubated at 0° C. for 30 minutes, transferred to three 36 ml tubes, and centrifuged at 39,000 g (14,726 rpm in a Sorval OTD ultracentrifuge containing a Sorval AH-627 rotor with 36 ml buckets) for 40 minutes at 0° to 4° C. Approximately 80 ml of supernatant was carefully transferred to a 500 ml glass conical flask and cofactor buffer was added. The solution was mixed and gently swirled in the 50° C. water bath until the temperature of the contents of the flask reached 30° C. Then the flask was immediately transferred to the 30° C. water bath where the incubation continued without further agitation for a total period of 20 minutes. The warm extract was transferred to six 17 ml plastic centrifuge tubes and centrifuged at 39,000 g (Sorval PTD centrifuge containing a Sorval AH-627 rotor with 17 ml buckets) for 40 minutes at 30° C. The supernatant was removed carefully with an aspirator and discarded. Each tube contained a pellet of approximately 140 mg of microtubule (MT) proteins (approximately 50% tubulin and 50% MAPS) and was stored at −70° C.

6.2. ISOLATION OF THE TAU CLASS OF MICROTUBULE ASSOCIATED PROTEINS FROM CYCLE PURIFIED MICROTUBULES

The total MAPS fraction of cycle purified microtubules was separated from tubulin by a modification of the method of Weingarten, (1975, *Proc. Natl. Acad. Sci. USA*, 72:1858–1862). A pellet of microtubules from the cycle purification method was resuspended using a small Dounce homogenizer in MES buffer (0.1M MES; 1 mM EGTA; 0.5 mM $MgCl_2$ and 1 mM β-mercaptoethanol) so that the resulting solution had an absorbance at 280 nm of 2.0–2.5 and then depolymerized by incubation for 30 min at 0° C. The resulting solution was centrifuged at 100,000 g for 1 hour and the pellet discarded. The supernatant was filtered through a 0.2μ milipore filter and applied to a phosphocellulose column (1.1 cm diameter×2.6 cm length, 2.5 ml bed volume) that had previously been equilibrated in MES buffer. Tubulin was eluted with MES buffer in the void volume of the column and when the absorbance of the eluate had returned to the baseline value, the total MAPS fraction was eluted (either 0.1 or 0.2 ml fractions) with MES buffer containing 1.0M NaCl and collected as a single complex peak of UV-absorbing material that contained multiple proteins.

The total MAPS fraction eluted from the phosphocellulose column was immediately desalted using the rapid Sephadex G-25 centrifugation method of Penefsky (*J. Biol. Chem.*, 1977, 252:2891–2899). The desalted total MAPS fraction was stirred at 0° C. and solid ammonium sulphate added until its conentration reached 35% (w/v). The stirring was continued for 30 minutes and then the suspension was centrifuged at 20,000 g for 15 minutes. The supernatant was removed and again stirred at 0° C. and more solid ammonium sulphate added until its concentration reached 45% (w/v). After a further 15 minute stirring the suspension was again centrifuged at 20,000 g for 15 minutes and the supernatant discarded. The pellet from this last centrifugation step was dissolved in Mes buffer and applied to a column of hydroxyapatite (1 cm dia×10 cm length) and eluted with Mes buffer. The fractions containing only four closely spaced peptides of apparent Mr 45,000 to 65,000 by SDS-PAGE were combined. This total eluted tau fraction was reduced to a volume of 1.0 ml with a sartorius collodion membrane operated in water under reduced pressure, according to the instructions of the manufacturer, and then divided into 0.1 ml portions in 0.5 ml plastic minifuge tubes and stored at −20 C.

The invention is not limited to the embodiments described herein and may be modified or varied without departing from the scope of the invention.

What is claimed is:

1. A method for confirming a clinical diagnosis of Alzheimer's Disease in a patient suspected of having Alzheimer's Disease, comprising performing an assay to determine the concentration of tau-peptide in the patient's blood, wherein the assay comprises contacting a sample of blood obtained from the patient with an antibody which specifically binds tau-peptide or a Fab fragment which specifically binds tau-peptide, wherein further the tau-peptide is derived from the amino terminal 200 animo acids or carboxy terminal 50 amino acids of a tau-protein; and determining the concentration of tau-peptide wherein an elevated concentration of tau-peptide confirms the clinical diagnosis of Alzheimer's Disease.

2. The method of claim 1, wherein the assay comprises an assay selected from the group consisting of a radioimmunoassay, an enzyme-linked immunosorbant assay, a sandwich assay, a precipitin reaction, a gel immunodiffusion assay, an agglutination assay, a fluorescent immunoassay, a protein A immunoassay and an immunoelectrophoresis assay.

* * * * *